United States Patent
Pinhack

(10) Patent No.: US 8,356,933 B2
(45) Date of Patent: Jan. 22, 2013

(54) CALORIMETER WITH A DIGESTION CONTAINER AND WITH A WATER JACKET

(75) Inventor: Hubert Pinhack, Bad Krozingen (DE)

(73) Assignee: IKA-Werke GmbH & Co. KG, Staufen (DE)

( * ) Notice: Subject to any disclaimer, the term of this patent is extended or adjusted under 35 U.S.C. 154(b) by 428 days.

(21) Appl. No.: 12/745,336

(22) PCT Filed: Nov. 20, 2008

(86) PCT No.: PCT/EP2008/009818
§ 371 (c)(1),
(2), (4) Date: Jun. 1, 2010

(87) PCT Pub. No.: WO2009/068219
PCT Pub. Date: Jun. 4, 2009

(65) Prior Publication Data
US 2010/0316087 A1 Dec. 16, 2010

(30) Foreign Application Priority Data
Nov. 29, 2007 (DE) .......................... 10 2007 057 463

(51) Int. Cl.
*G01K 17/00* (2006.01)
*G01N 25/26* (2006.01)
*G01N 25/44* (2006.01)
(52) U.S. Cl. .............................. 374/33; 422/51; 436/147
(58) Field of Classification Search .................... 374/33; 422/51; 436/147
See application file for complete search history.

(56) References Cited

U.S. PATENT DOCUMENTS

| 2,733,602 | A | * | 2/1956 | Jackson, Jr. et al. | 374/33 |
| 3,718,437 | A | * | 2/1973 | Paloniemi | 422/51 |
| 4,511,263 | A | * | 4/1985 | Prosen | 374/38 |
| 4,616,938 | A |   | 10/1986 | Bonnard |  |
| 5,547,282 | A | * | 8/1996 | Pinhack et al. | 374/36 |
| 5,813,763 | A | * | 9/1998 | Plotnikov et al. | 374/11 |
| 6,627,451 | B2 | * | 9/2003 | Pinhack et al. | 436/147 |
| 7,712,956 | B2 | * | 5/2010 | Richner et al. | 374/43 |
| 8,262,989 | B2 | * | 9/2012 | Carlsson et al. | 422/51 |
| 2005/0008063 | A1 | * | 1/2005 | Chippett | 374/34 |
| 2010/0255588 | A1 | * | 10/2010 | Schenker | 436/43 |

FOREIGN PATENT DOCUMENTS

| DE | 4314454 | 10/1994 |
| DE | 19542138 | 10/1996 |
| DE | 10024147 | 10/2001 |
| GB | 2089507 | 6/1982 |

* cited by examiner

*Primary Examiner* — Christopher Fulton
(74) *Attorney, Agent, or Firm* — Volpe and Koenig, P.C.

(57) ABSTRACT

A calorimeter (1) with a decomposition chamber (3) with a combustion chamber (2), in which a receiving device (4) for a sample, an ignition device (5), and at least one supply line (6) for oxygen are provided. The decomposition chamber (3) is surrounded by a liquid or water jacket (7) into which at least one temperature sensor (8) extends. The liquid or water jacket (7) is surrounded by an outer container (9), which is a pressure container and which absorbs pressure generated during the combustion of a sample in the decomposition chamber (3) at the walls (10) thereof as a result of a tight sliding fit (15) by way of the water or the incompressible liquid. The decomposition chamber (3) therefore has an accordingly thin wall so that the heat generated during combustion of a sample can reach the temperature sensor or sensors (8) quickly.

14 Claims, 2 Drawing Sheets

CALORIMETER WITH A DIGESTION CONTAINER AND WITH A WATER JACKET

BACKGROUND

The invention relates to a calorimeter with a decomposition vessel that contains a combustion chamber and in which a holder device for a sample and an ignition device, as well as at least one supply line for oxygen are provided, with a water jacket or liquid jacket surrounding the decomposition vessel, a temperature sensor projecting into the water or liquid jacket, and with an outer vessel encompassing the water or liquid jacket.

Such calorimeters are known in many forms, for example, from DE 43 14 454 C1 or DE 100 24 147 C1. So that the internal pressure produced during the combustion of a sample does not lead to destruction, the decomposition vessel containing the combustion chamber must have a thick and stable jacket and must also be made from high-quality material, so that it cannot disrupt or influence the combustion and is not damaged itself.

In practice it has been shown that, for a calorimetric measurement, in the normal case, for example, twenty minutes of time are needed, because initially the corresponding heat must be transferred through the thick-walled decomposition vessel into the water jacket and must be distributed there. Simultaneously, previously known calorimeters are relatively complicated and correspondingly expensive, because insulation is also required outside of the vessel wall containing the water or the liquid, in order to rule out environmental influences on the measurement result at least to a large degree.

SUMMARY

Therefore, the objective arises of creating a calorimeter of the type noted above in which, above all, the time for performing a measurement is as short as possible.

To meet this objective, in the calorimeter defined above it is provided that the outer vessel is constructed as a pressure vessel and receives the pressure produced on its walls during a combustion in the pressure-yielding decomposition vessel via the water jacket or liquid jacket, called "water jacket" below for the sake of simplicity, and that, for compensating for heat movements and pressure differences, the walls of the decomposition vessel are connected to its base by a tight, pressure-yielding, close sliding fit or a membrane, bellows, or a moving piston is arranged on the decomposition vessel.

Through such an arrangement it is possible for the decomposition vessel containing the combustion chamber to have a thin-walled construction, because the pressure produced during the combustion in this pressure-yielding, optionally volume-changing decomposition vessel is led via the incompressible fluid or the incompressible water to the outer-lying pressure vessel and is received by this vessel, so that the heat transfer from the decomposition vessel into the water can take place quickly. The measurement process requires a correspondingly small amount of time. Simultaneously, less of the relatively expensive material is needed for the decomposition vessel.

Thus the invention allows the decomposition vessel to have a thin-walled construction in relationship to the outer-lying pressure vessel and its wall thickness is less than the wall thickness of the pressure vessel.

A preferred construction of the invention provides that the inside of the walls of the pressure vessel are provided with insulation for isolation against external influences and for reducing the energy transport from the decomposition vessel via the incompressible fluid or water surrounding it to or into the pressure vessel. Therefore it can be achieved that, indeed, the fluid or the water, but not the pressure vessel, is heated, which could falsify the measurement. Thus, the pressure vessel could indeed collect the pressure occurring during the combustion of a sample, but is itself only slightly heated and, together with the insulation located on its inner side, keeps away external influences from the water jacket, so that resulting falsifications of the measurement result are avoided at least to a large degree.

It is preferred when the insulation is an insulating vessel. This could be preassembled in a simple and preferable way and then inserted into the outer vessel.

A preferred construction, above all, for the insulation can provide that the insulation or the insulating vessel is spaced away from the inside of the pressure vessel or contacts the inside of the pressure vessel only at some positions. In this way, an insulating space that improves the insulating effect can remain between the pressure vessel and the insulation.

Between the pressure vessel and insulation or insulating vessel there can be spacers and/or deformations, such as ribs, nubs, or the like on one or two of the vessels. In this way, the pressure also acting on the insulation can be better transmitted to the outer container or pressure vessel during the combustion of a sample. Simultaneously, these spacers could be dimensioned with respect to cross section and dimensions so small that no significant quantities of heat could be transferred via these spacers.

At least the decomposition vessel can be made from a temperature-resistant and/or chemical-resistant material, for example, metal, ceramic, and/or plastic. Even plastic is possible because the decomposition vessel itself does not have to receive any pressure, but instead transfers this via the water jacket to the outer pressure vessel.

The pressure vessel and/or the insulating vessel can be made from metal, ceramic, and/or plastic. Here, the material selection can be made on what samples are usually to be combusted and examined.

An additional construction of the invention can provide that insulation or an insulating sleeve is arranged on the outside of the pressure vessel. This can be used for improving the exclusion of external influences. In addition, in this way an insulating vessel within the pressure vessel could be avoided or spared.

In the space filled up by the incompressible fluid or the water during use between the decomposition vessel and the pressure vessel, there can be at least one device for moving the fluid or a stirrer. In this way, the distribution of the heat generated during the combustion of a sample can be accelerated.

It is especially favorable when a magnetic stirrer is provided or arranged in the space of the calorimeter filled up during use by the incompressible fluid or water.

The fluid agitation performed for rapid heat equalization in this space or intermediate space thus can be performed with the moveable part of a magnetic stirrer that can be driven magnetically. In this way, the agitation movement for the high pressures generated by the combustion is possible without a lead-through, such as a shaft or the like, to the outside. Furthermore, the heat development that influences the calorimetric process and that is produced due to sliding friction of such a shaft requiring a seal that is effective against high pressure is avoided.

In the intermediate space that is arranged between the decomposition vessel and the pressure vessel and that receives water or an incompressible fluid during use, there can optionally be more than one temperature measurement sensor, wherein these multiple temperature measurement sensors can advantageously be distributed in a uniform arrangement. In this way, the measurement speed and the measurement accuracy can be increased.

For balancing the energy, one or more temperature measurement sensors can be arranged on the outside of the pressure vessel. In this way it can be tested whether and how much heat is possibly also discharged through the pressure vessel or what temperature difference exists between the two sides of the walls of the pressure vessel.

An additional construction of the invention provides that a heating device for setting a constant temperature of the pressure vessel on the pressure vessel. In this way it can be achieved that external influences are excluded in the measurement.

The shape of the combustion chamber within the decomposition vessel can be arbitrary and is curved at least across a partial region or cylindrical across the entire height or constructed as a bellows, in order to allow a space-saving shape, wherein, however, pressure resistance does not have to be taken into account, because the pressure is advantageously transmitted via the fluid jacket to the outer vessel used as the pressure vessel.

Primarily for the combination of individual or several of the features and measures described above, it is produced, in particular, that the pressure generated by the combustion of a sample is received by the vessel that also bounds the water or fluid jacket on the outside, so that the entire calorimeter can be produced with a space-saving construction, that is, with a significantly smaller total volume than conventional calorimeters. Its transport is lightweight and simple accordingly and short calorimetric measurements can also be performed quickly accordingly at different positions or locations. Here, due to the incompressibility of the fluid, a slight compression under loading or optionally slight expansion of the decomposition vessel can be sufficient.

BRIEF DESCRIPTION OF THE DRAWINGS

Embodiments of the invention will be described in detail below with reference to the drawing. Shown in greatly schematized representation are.

DETAILED DESCRIPTION OF THE PREFERRED EMBODIMENTS

Figure 1:
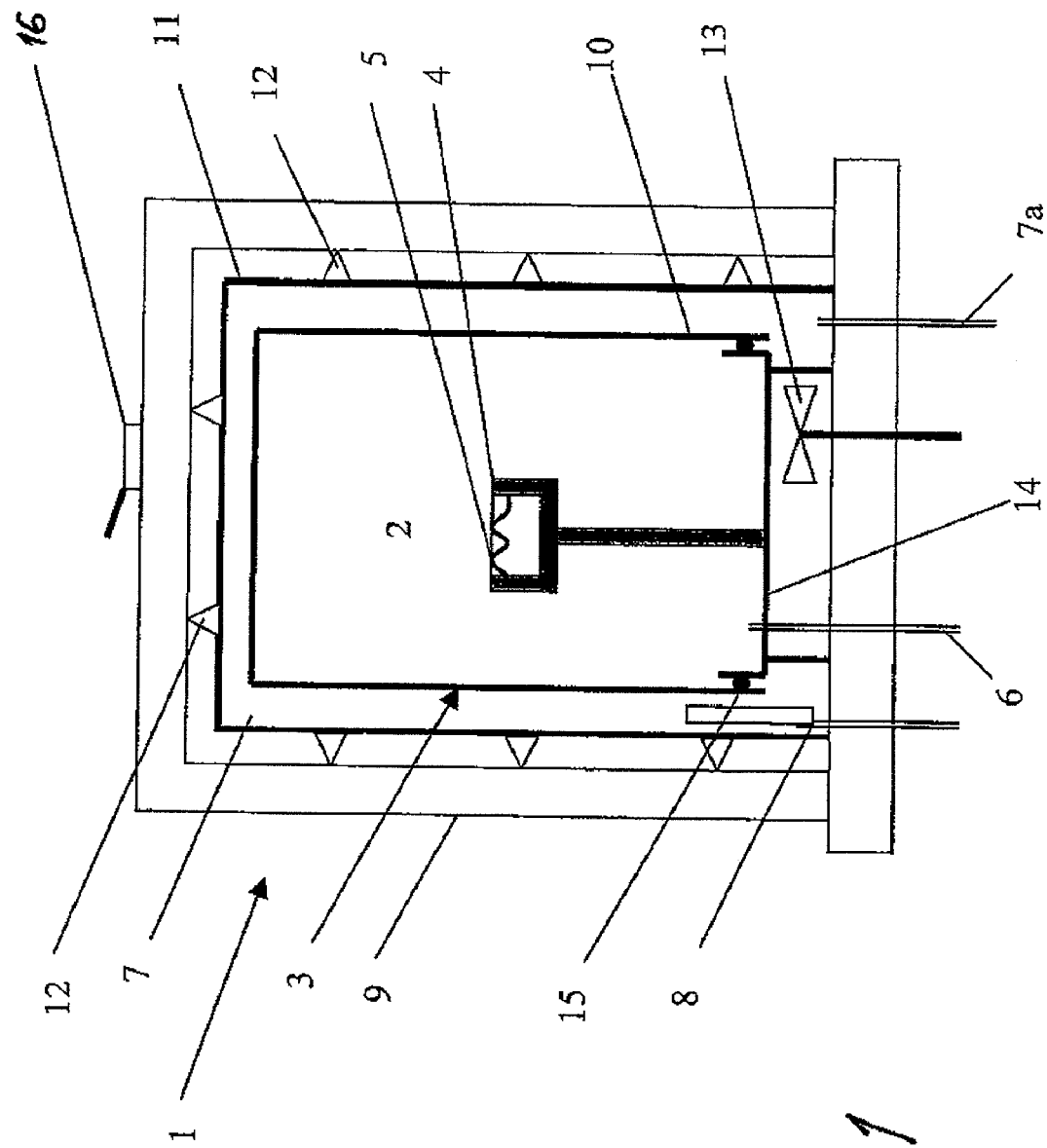
FIG. 1 a vertical section view through a first embodiment of a calorimeter according to the invention and FIG. 2 a view of a second embodiment of the calorimeter according to the invention corresponding to FIG. 1.

In the following description of two embodiments, parts that have matching functions are given matching reference symbols, even if they have modified constructions.

A calorimeter designated overall with 1 is used for measuring the heat of combustion of substances and has, for this purpose, a decomposition vessel 3 that contains a combustion chamber 2 and in which a holder device 4 for such a sample and an ignition device 5, as well as a supply line 6 for oxygen are provided.

The decomposition vessel 3 is typically located in a water bath, that is, it is surrounded by a water jacket 7, wherein, instead of water, another incompressible fluid could also be provided. The supply line 7a to the water jacket 7 is provided in the base region.

A temperature measurement sensor 8 projects into this water jacket 7 or fluid jacket, in order to measure the heat generated by the combustion of a sample. Furthermore, an outer vessel 9 encompassing the water or fluid jacket 7 is provided.

In order to achieve the shortest possible measurement times and simultaneously also comparatively small dimensions, the outer vessel 9 is constructed as a pressure vessel and receives the pressure generated by combustion in the decomposition vessel 3 at its walls 10 via the fluid or water jacket 7, so that the walls 10 can have a relatively small thickness that influences the heat passage to a correspondingly small degree.

In the figures, one can see that the decomposition vessel 3 is constructed with thin walls in comparison with the outer vessel 9 constructed as a pressure vessel, wherein the wall thickness of the decomposition vessel 3 is significantly smaller than the wall thickness of the outer or pressure vessel 9, also called "pressure vessel 9" below.

In the embodiment according to FIG. 1, the inside of the walls of the pressure vessel 9 are provided with insulation that is an insulating vessel 11 in the embodiment thus containing the water jacket 7 for isolation from external influences that could disrupt the measurement accuracy and for reducing the energy transport from the decomposition vessel 3 via the water of the water jacket 7 surrounding it into the pressure vessel 9. One can clearly see that the insulation, that is, the insulating vessel 11 is spaced apart from the inside of the pressure vessel 9 and contacts the inside of the pressure vessel 9 via spacers 12 only in some positions. The spacing formed between the insulating vessel 11 and outer vessel 9 can reinforce the isolation.

Figure 2:
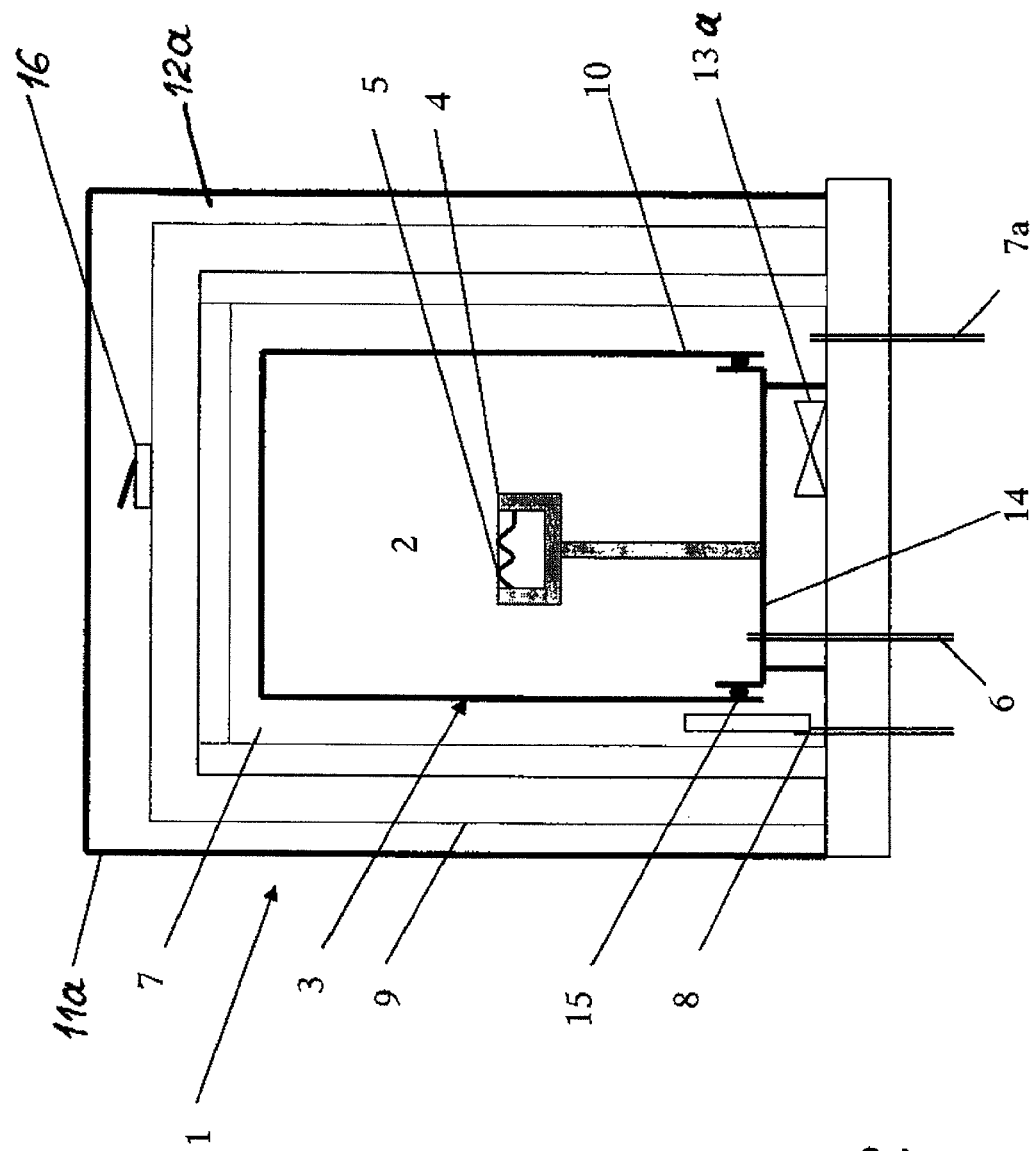

In the embodiment according to FIG. 2, it is provided that insulation or an insulating sleeve 11a is arranged on the outside of the pressure vessel 9, so that an insulating vessel 11 can be eliminated within the pressure vessel 9. Here, one can see an air gap 12a that forms, together with the insulating sleeve 11a, the outer insulation between this insulating sleeve 11a and the pressure vessel 9. In this way, an energy transport from the pressure vessel or outer vessel 9 to the surroundings can be reduced.

It should be mentioned that at least the decomposition vessel 3, but preferably also the pressure vessel 9 and optionally the insulating vessel 11 could be made from a temperature-resistant and/or chemically resistant material, for example, from metal, ceramic, and/or plastic, by means of which weight is saved. In a way that is not shown, insulation or an insulating sleeve could be arranged on the outside of the pressure vessel 9, in order to avoid external influences even better. In the space filled by the incompressible fluid or water during use, that is, in the water jacket 7, in the embodiment according to FIG. 1, a device for moving the fluid or the water, namely a stirrer 13 is provided with which the water can be moved accordingly and therefore the prevailing or elevated temperature can be distributed quickly and uniformly.

A device for moving the fluid or the water, in this case, a magnetic stirrer 13a, is also provided in the embodiment according to FIG. 2 in the space filled by the incompressible fluid or the water during use, that is, in the water jacket 7. The fluid or the water is similarly moved with this device for moving the fluid or water and therefore the prevailing or elevated temperature can be distributed quickly and uniformly. In contrast to the embodiment according to FIG. 1, however, no drive shaft is needed for the actual stirrer element, because the magnetic stirrer 13 can be driven in a known way without contact by a magnetic coupling.

More than one temperature measurement sensor 8 could possibly also be provided, in order to be able to detect the change in temperature quickly and, in this way, possible temperature differences.

It should also be mentioned that the walls 10 of the decomposition vessel 3 are connected to its base 14 by a tight sliding fit 15 for equalizing movements due to heat and pressure differences. The pressure equalization can also be performed by a membrane, a bellows, or a moving piston arranged on the decomposition vessel.

For balancing the energy, on the outside of the pressure vessel 9 there can be an additional temperature measurement sensor 16 that is provided, in this way, on the top side in the embodiment. In a way not shown in detail, a heating device for setting a constant temperature of the pressure vessel 9 could be provided on the pressure vessel 9, in order to exclude external influences on the measurement result.

The calorimeter 1 has a decomposition vessel 3 with combustion chamber 2 in which a holder device 4 for a sample and an ignition device 5, as well as at least one supply line 6 for oxygen, are provided. The decomposition vessel 3 is surrounded by a fluid or water jacket 7 into which at least one temperature measurement sensor 8 projects. The fluid or water jacket 7 is encompassed by an outer vessel 9 that is constructed as a pressure vessel and that receives the pressure generated by the combustion of a sample in the decomposition vessel 3 at its walls 10 due to the tight sliding fit 15 via the water or the incompressible fluid. The decomposition vessel 3 can have a corresponding thin-walled construction, so that the heat generated by the combustion of a sample is led in a corresponding quick way to the temperature measurement sensor or sensors 8.

The invention claimed is:

1. Calorimeter (1) comprising a pressure-yielding decomposition vessel (3) that contains a combustion chamber (2) and in which a holder device (4) for a sample and an ignition device (5) are located, at least one supply line (6) is provided for oxygen, a fluid or water jacket (7) surrounds the decomposition vessel (3), at least one temperature measurement sensor (8) projects into the fluid or water jacket (7), and an outer vessel (9) encompasses the fluid or water jacket (7), the outer vessel (9) is constructed as a pressure vessel and receives pressure produced on its walls due to combustion in the pressure-yielding decomposition vessel (3) via the fluid or water jacket (7), and, for equalizing movements due to heat and pressure differences, the walls (10) of the decomposition vessel (3) are connected to its base (14) via a tight, pressure-yielding sliding fit (15), or a membrane, a bellows, or a moving piston is arranged on the decomposition vessel (3).

2. Calorimeter according to claim 1, wherein the decomposition vessel (3) has a thin-walled construction in comparison with the outer vessel and a wall thickness of the decomposition vessel is less than a wall thickness of the outer vessel (9).

3. Calorimeter according to claim 1, wherein an inside of the walls of the outer vessel (9) is provided with insulation for isolation from external influences and for reducing energy transport from the decomposition vessel (3) via the water surrounding it into the outer vessel (9).

4. Calorimeter according to claim 3, wherein the insulation of the pressure outer vessel (9) comprises an insulating vessel (11).

5. Calorimeter according to claim 4, wherein the insulating vessel (11) is at least one of spaced away from an inside of the outer vessel (9) or contacts the inside of the outer vessel (9) only in some positions.

6. Calorimeter according to claim 5, wherein at least one of spacers (12) or deformations which are arranged on one or both of the vessels are provided between the outer vessel (9) and the insulation or insulating vessel (11).

7. Calorimeter according to claim 1, wherein at least the decomposition vessel (3) is made from at least one of a temperature-resistant or chemically resistant material.

8. Calorimeter according to claim 1, wherein at least one of the outer vessel (9) or the insulating vessel (11) is made from at least one of metal, ceramic, or plastic.

9. Calorimeter according to claim 1, wherein insulation or an insulating sleeve is arranged on an outside of the outer vessel (9).

10. Calorimeter according to claim 1, wherein at least one device for moving fluid or a stirrer (13) is provided in a space defined by the fluid or water jacket that is filled by an incompressible fluid or water during use.

11. Calorimeter according to claim 1, wherein a magnetic stirrer is provided in a space defined by the fluid or jacket (7) that is filled by an incompressible fluid or water during use.

12. Calorimeter according to claim 1, wherein more than one temperature measurement sensor (8) is provided in an intermediate space that is arranged between the decomposition vessel (3) and the outer vessel (9) and that holds water or an incompressible fluid during use.

13. Calorimeter according to claim 1, wherein for balancing energy, one or more temperature measurement sensors (16) are arranged on an outside of the outer vessel (9).

14. Calorimeter according to claim 1, wherein at least one heating device is provided on the pressure vessel (9) for setting a constant temperature of the outer vessel (9).

* * * * *